US00PP14513P29

(12) United States Plant Patent
Warren et al.

(10) Patent No.: US PP14,513 P2
(45) Date of Patent: Feb. 3, 2004

(54) CALLA LILY PLANT NAMED 'POT BLACK'

(50) Latin Name: *Zantedeschia spp.*
Varietal Denomination: Pot Black

(75) Inventors: Andrew G. F. Warren, Tauranga (NZ); Jacobus J. P. Spaans, Tauranga (NZ)

(73) Assignee: Bloomz Limited, Tauranga (NZ)

( * ) Notice: Subject to any disclaimer, the term of this patent is extended or adjusted under 35 U.S.C. 154(b) by 0 days.

(21) Appl. No.: 10/383,009

(22) Filed: Mar. 6, 2003

(51) Int. Cl.[7] ..... A01H 5/00
(52) U.S. Cl. ..... Plt./263

(58) Field of Search ..... Plt./263

(56) References Cited

U.S. PATENT DOCUMENTS

PP11,001 P * 7/1999 Spaans ..... Plt./263

* cited by examiner

*Primary Examiner*—Bruce R. Campell
*Assistant Examiner*—Susan B. McCormick
(74) *Attorney, Agent, or Firm*—Jondle & Associates, PC

(57) ABSTRACT

A calla lily potted plant particularly distinguished by dark purple/black spathe and lightly maculated leaves.

3 Drawing Sheets

Genus and species: *Zantedeschia spp.*
Variety denomination: 'Pot Black'.

BACKGROUND OF THE NEW PLANT

The present invention comprises a new and distinct cultivar of calla lily, botanically known as *Zantedeschia spp,* and hereinafter referred to by the cultivar name 'Pot Black'. The new cultivar is asexually reproduced from vegetative cuttings and tissue culture resulting from the cross of the seed parent a dark purple seedling that is a proprietary line that is unnamed and unpatented×'Chianti' not patented.

'Pot Black' is a product of a planned breeding program intended to create new calla lily pot plants with with a deep burgundy spathe.

The new cultivar was created in 1998 in Tauranga New Zealand and has been asexually reproduced repeatedly by vegetative cuttings and tissue culture in New Zealand over a 3 year period. The present invention has been found to retain its distinctive characteristics through successive propagations; and this novelty is firmly fixed.

DESCRIPTION OF PHOTOGRAPH

This new calla lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
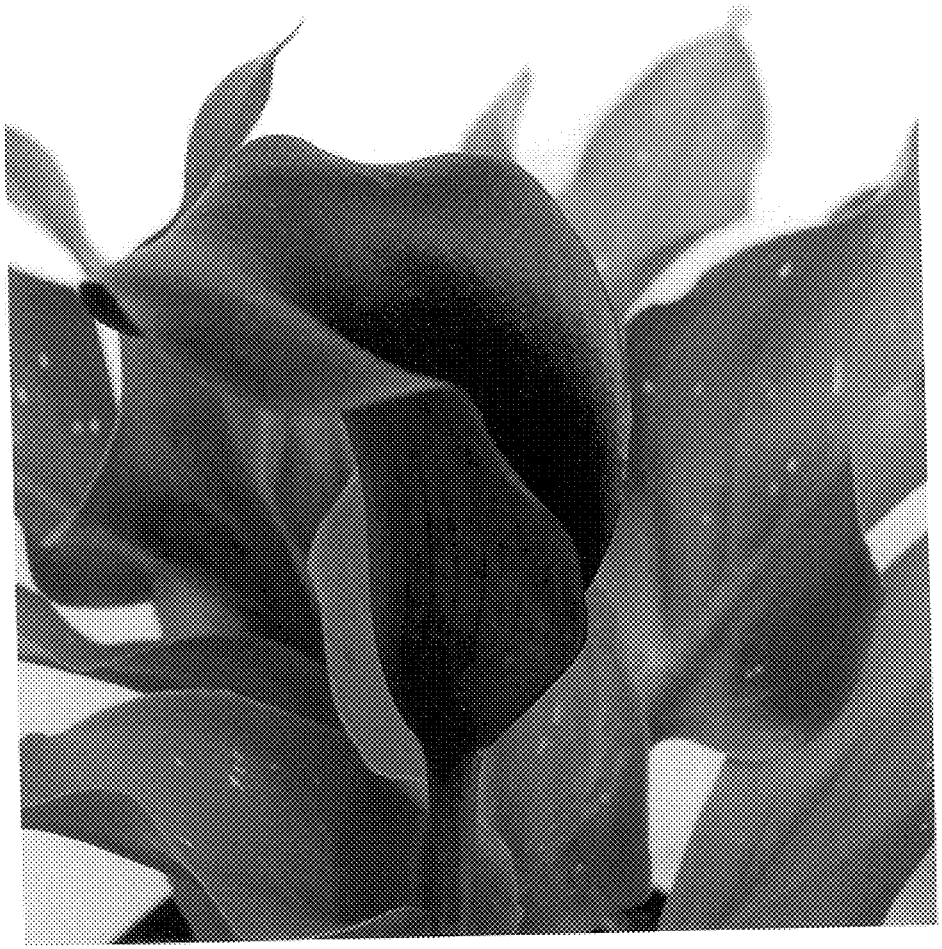
FIG. 1 shows the mature inflorescence.
Figure 2:
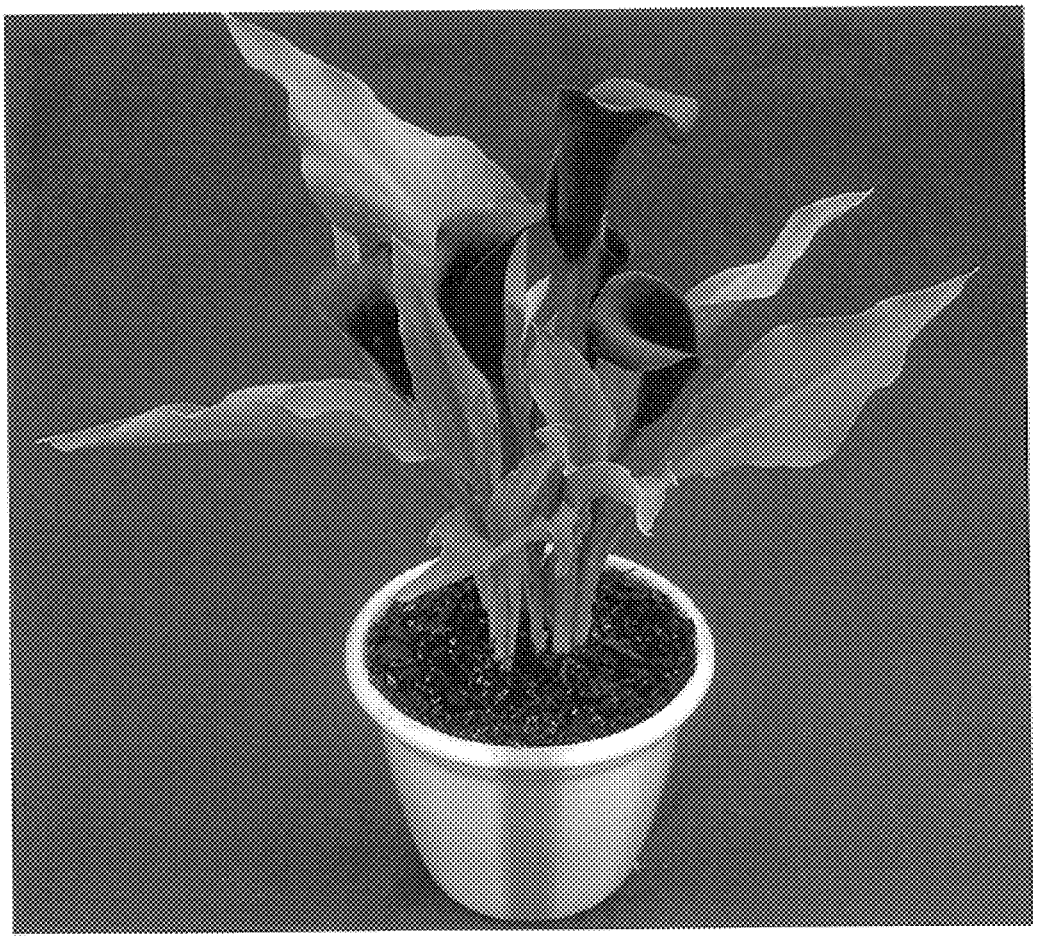
FIG. 2 shows the overall plant habit.
Figure 3:
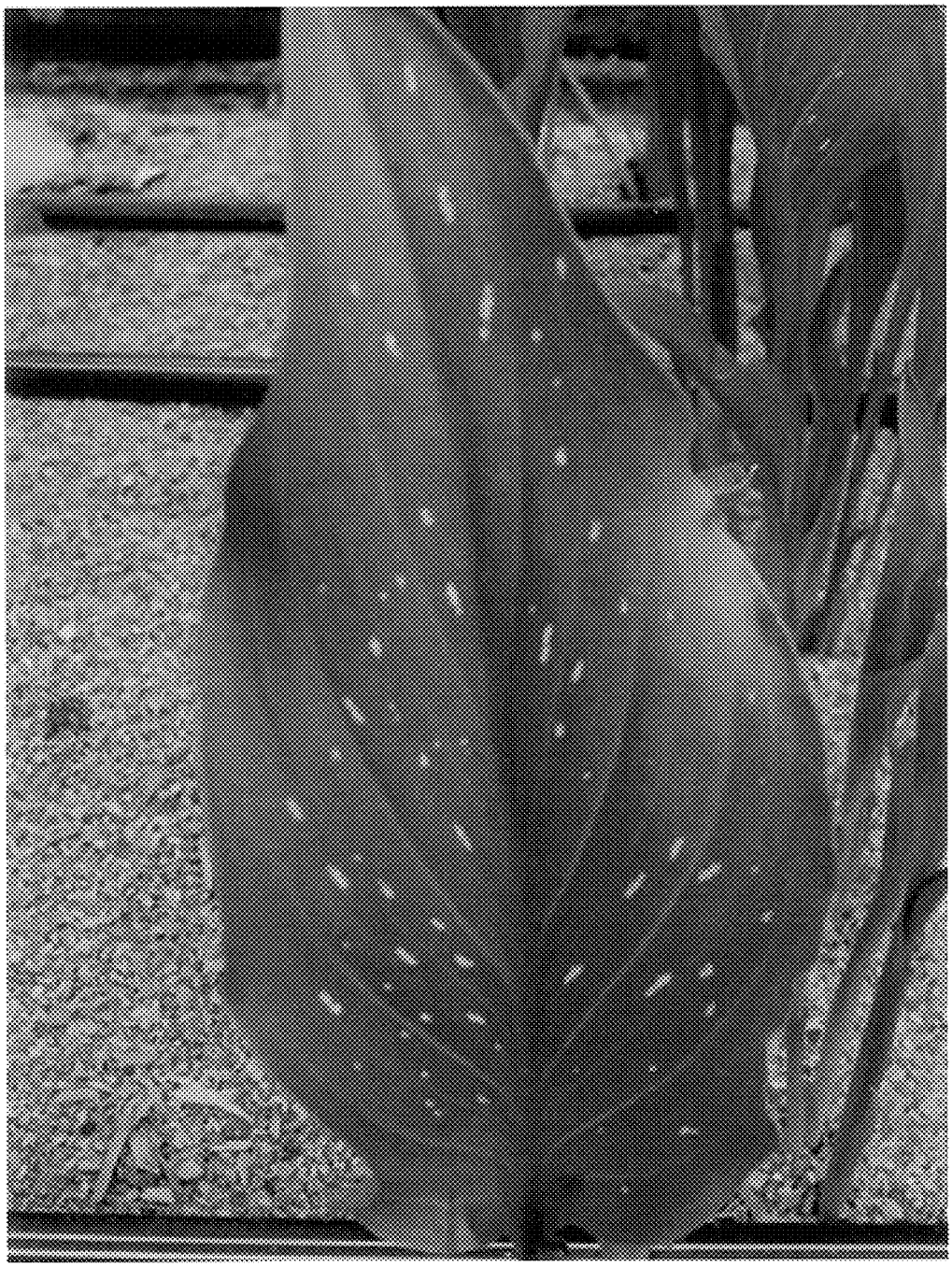
FIG. 3 shows the leaves.

The following detailed descriptions set forth the distinctive characteristics of 'Pot Black'. The data which defines these characteristics were collected from asexual reproductions carried out in New Zealand. The plant history was taken on 2 year old plants based on a 3 cm diameter tuber under New Zealand Spring conditions. Color references are primarily to The R.H.S. Colour Chart of The Royal Horticultural Society of London (R.H.S).

THE PLANT

Classification:
- *Botanical.*—*Zantedeschia spp.*
- *Commercial.*—Calla lily.
- *Variety.*—'Pot Black'.

Size:
- *Form.*—Erect.
- *Height of the leaf canopy above the soil.*—20–30 cm.
- *Height of top of inflorescence above the soil.*—20–30 cm.
- *Diameter.*—15–25 cm.
- *Number of inflorescence per tuber size.*—Tuber diameter 3 cm 2–4. Tuber diameter 4 cm 4–6. Tuber diameter 5 cm 6+.

Branches:
- *Character.*—Strong.
- *Color.*—Upper is green RHS 144A; lower is green RHS 144B; base is white RHS 155C.
- *Average number.*—3–4.

Leaves:
- *Size.*—Width 5–10 cm; length 10–20 cm.
- *Shape.*—Ovate.
- *Color.*—Upper is green RHS 137A; lower is green RHS 137B.
- *Maculation* (*leaf spots*).—Low density; white RHS 155C.
- *Apex.*—Acute to apiculate.
- *Margin.*—Moderately wavy.
- *Margin color.*—Yellow-Green RHS 145A.
- *Veins.*—Pinnate
- *Surface quality.*—Leathery.

Petiole (leaf stalk):
- *Length.*—10–15 cm.
- *Color.*—Base is Green RHS 144B; upper is green RHS 144A.

Roots:
- *Color.*—White.

*Branching.*—Not branched, attached to the top of the tuber at the apices.

*Disease resistance.*—No susceptibility noted to date.

*Pest resistance.*—No susceptibility noted to date.

THE INFLORESCENCE

Spathe (flower body):

*Size.*—Length 6–10 cm; width 3–4 cm.

*Color.*—Upper is dark purple RHS 187A to black RHS 202A; lower is dark purple RHS 81A.

*Veins.*—Present, black RHS 202A.

*Shape.*—Fluted.

Spadix (reproductive organs):

*Size.*—Length 2.5–3 cm; diameter 0.5–1.0 cm.

*Color.*—Base is dark purple RHS 187A; Upper is dark purple RHS 187A.

*Position relative to spathe.*—Upright.

Peduncle (flower stem):

*Size.*—20–30 cm.

*Color.*—Green RHS 144B; upper is Green RHS 144A.

Reproductive organs:

*Location of female organs.*—Basal position of the spadix.

*Location of male organs.*—Upper position of the spadix Perianth (the floral envelope — calyx and corolla) Conspicuous.

*Stamens.*—Not visible before pollen release.

*Pistil.*—30–35 per spadix; yellow-green RHS 150C.

Miscellaneous:

*Time to produce a finished flowering plant.*—6–10 weeks.

*Lastingness.*—2–3 weeks.

*Fragrance.*—None.

*Fruit.*—None.

*Production.*—30–35 berries.

*Color.*—Predominantly purple RHS 187A with green markings RHS 143A.

COMPARISON WITH KNOWN CULTIVARS

When the instant plant is compared to 'Ruby Light Red' (patent status unknown) the 'Pot Black' foliage has a low density of maculation and the shape of the leaves are ovate. Additionally the flower color is a different color than 'Ruby Light Red'.

I claim:

1. A new and distinct cultivar of calla lily plant as shown and described herein.

* * * * *